United States Patent [19]

Hagen et al.

[11] 4,385,521

[45] May 31, 1983

[54] ULTRASONIC APPARATUS FOR SECTOR SCANNING

[75] Inventors: Jürgen Hagen; Walter Hetz; Gert Hetzel, all of Erlangen; Dirk Schroeder, Eckental, all of Fed. Rep. of Germany

[73] Assignee: Siemens Aktiengesellschaft, Berlin & Munich, Fed. Rep. of Germany

[21] Appl. No.: 191,450

[22] Filed: Sep. 29, 1980

[30] Foreign Application Priority Data

Oct. 16, 1979 [DE] Fed. Rep. of Germany ....... 2941876

[51] Int. Cl.³ .............................................. G01N 29/04
[52] U.S. Cl. ......................................... 73/619; 73/633
[58] Field of Search .................... 73/633, 619; 128/660

[56] References Cited

U.S. PATENT DOCUMENTS

| | | | |
|---|---|---|---|
| 4,034,744 | 7/1977 | Goldberg | 128/660 |
| 4,106,492 | 8/1978 | Schuette et al. | 73/633 |
| 4,151,834 | 5/1979 | Sato et al. | 73/619 |

OTHER PUBLICATIONS

Matzuk et al., "Novel Ultrasonic Real-Time Scanner featuring Servo Controlled Transducers Displaying a Sector Image", *Ultrasonics*, Jul. 1978.

Primary Examiner—Anthony V. Ciarlante
Attorney, Agent, or Firm—Hill, Van Santen, Steadman, Chiara & Simpson

[57] ABSTRACT

In the exemplary embodiments, the apparatus comprises: an ultrasonic transducer arrangement; a drive arranged to pivotably displace the transducer arrangement within a predetermined angular range; an actual-value generator for supplying a signal ($F_I(\varphi)$) dependent upon the angular position of the transducer arrangement within the said range; a desired-value generator for supplying a signal ($F_S(\varphi)$) representing a desired angular position of the transducer arrangement within the said range; and a control for controlling the drive in dependence upon such signals from the actual-value and desired-value generators. The actual-value and desired-value generators are adapted to supply respective signals having the same or similar forms over a relatively large signal range within the said range.

7 Claims, 11 Drawing Figures

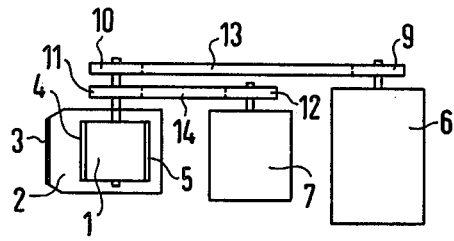
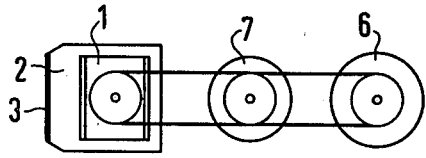
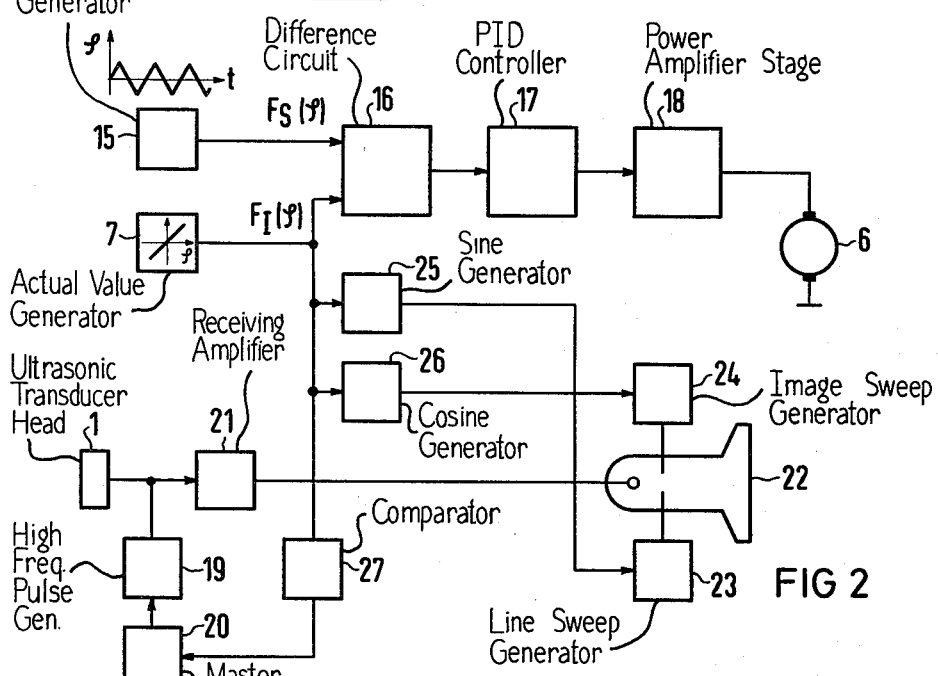
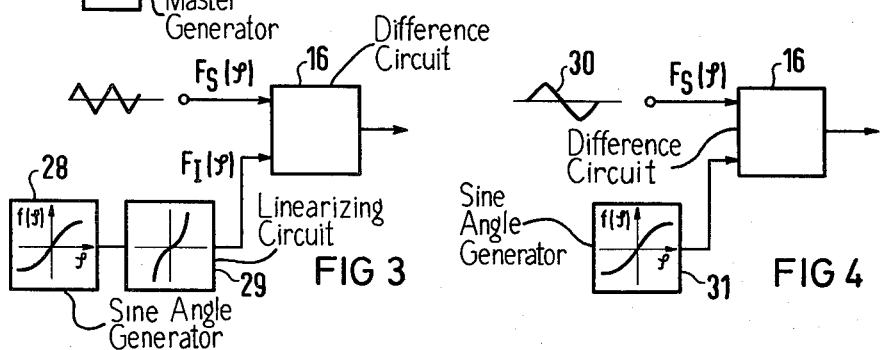

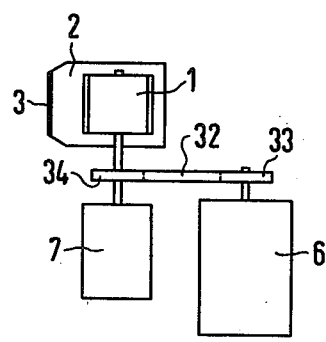 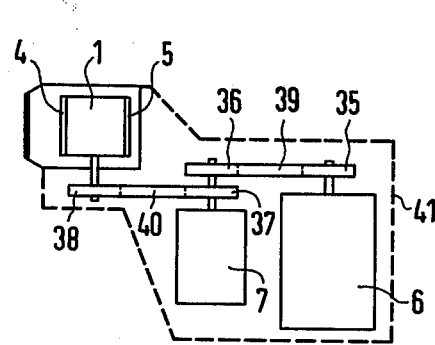
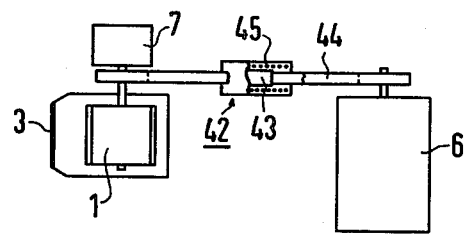
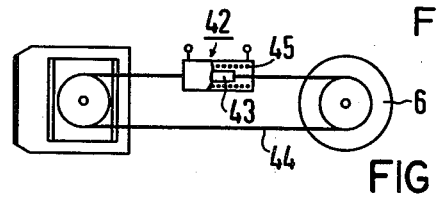 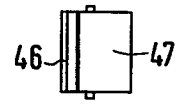
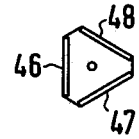

ULTRASONIC APPARATUS FOR SECTOR SCANNING

BACKGROUND OF THE INVENTION

This invention relates to ultrasonic scanning apparatus.

The applicator of a mechanical ultrasonic, sector scanner, more particularly of one for ultrasonic tomographic examination of the human heart, should ideally be such that the sound head thereof can be moved at a presettable, more particularly constant, angular velocity. In addition, the course of the displacement, the image frequency and the maximum angle should be readily variable by electronic control. Also, it should be possible, more particularly for heart-phase-triggered individual-image photography, to run-up the sound head from a position of rest to a desired, more particularly constant, angular velocity in a minimum time. A further requirement is that the drive should always lie outside the liquid used, for example, as a lead path, and it should have a long useful life, while in addition it should be possible to change the sound head readily and rapidly. At the same time, it is desirable for the applicator always to be of small overall dimensions and compact, as well as being light and possibly bent over at an angle, so that it can be readily applied regardless of the position of the body. Driving systems are described, for example, in German Offenlegungsschrift Nos. 27 50 160, 22 16 577, German Auslegeschrift No. 26 01 559, German Patentschrift No. 25 29 155, U.S. Pat. No. 4,034,744, and "Ultrasonics", July, 1978, pages 171 to 178. U.S. Pat. No. 4,106,492 also describes ultrasonic scanning apparatus. The ultrasonic scanning apparatus described in U.S. Pat. No. 4,106,492 only permits pivoting angles of the sound head in the range from 0° to ±25°. In the apparatus described therein there are compared with one another, by way of actual-value/desired-value comparison for the sound head angular position, two functions which differ appreciably from one another in configuration. Thus, a sine function occurring as an actual-value signal is compared with a triangular function occurring as a desired-value signal, which signals have equality of form only for small angles, i.e. in a very small signal range.

SUMMARY OF THE INVENTION

According to the invention there is provided ultrasonic scanning apparatus comprising: an ultrasonic transducer arrangement; drive means arranged to pivotably displace the transducer arrangement within a predetermined angular range; an actual-value generator for supplying a signal dependent upon the angular position of the transducer arrangement within the said range; a desired-value generator for supplying a signal representing a desired angular position of the transducer arrangement within the said range; and control means for controlling the drive means in dependence upon such signals from the actual-value and desired-value generators; wherein the actual-value and desired value generators are adapted to supply respective signals having the same or similar forms over a relatively large signal range within the said range.

The control means preferably comprises a closed control loop.

The actual-value and desired-value generators could be adapted such that there is substantially direct proportionality between the position of the transducer arrangement, within the said range, and the respective signals supplied by the generators in use. In this case, the desired-value generator could be adapted to supply a substantially linear signal and the actual-value generator could be adapted to supply a substantially linear signal either throughout the said range or, at least, beyond the linear portion of a signal which would be supplied by a sine or cosine signal generator in its place. The actual-value generator could comprise a sine or cosine signal generator, an output of which is connected with a device for rendering substantially linear, signals supplied by the sine or cosine signal generator. Alternatively, the actual-value generator could comprise a substantially linear signal generator.

The actual-value generator could comprise a field-plate potentiometer or it could comprise a linear resolver.

Alternatively, the desired-value generator could comprise a sine or cosine function generator and the actual-value generator could comprise a sine or cosine function generator respectively.

The apparatus could further be provided with a clock signal generator for controlling the transmission of ultrasonic pulses from the transducer arrangement, the clock signal generator being controlled in use by signals produced by the actual-value generator such that master clock pulses are produced by the clock signal generator at predetermined steps between first and second predetermined amplitudes of signal produced by the actual-value generator.

The drive means preferably comprise a motor and step-up gearing arranged between the motor and the transducer arrangement. In this case, the step-up gearing could comprise a belt drive arrangement which is coupled, on the one hand, with the motor, and on the other hand, with the transducer arrangement and actual-value generator. This belt drive arrangement could comprise at least one toothed belt. In this case, the or each toothed belt is preferably coupled by a large number of teeth, on the one hand, with the motor, and on the other hand, with the transducer arrangement and actual-value generator.

The transducer arrangement preferably comprises a plurality of ultrasonic transducers which are adapted for rotation by the drive means such that any one transducer can form an active transducer of the transducer arrangement at any instant.

The invention will now be described, by way of example, with reference to the accompanying sheets of drawings; and other objects, features and advantages will be apparent from this detailed disclosure and from the appended claims.

BRIEF DESCRIPTION OF THE DRAWINGS

FIG. 1 (comprising FIGS. 1A and 1B) shows the construction of an ultrasonic applicator for ultrasonic scanning apparatus;

FIG. 2 shows a block circuit diagram of ultrasonic apparatus provided with the applicator shown in FIG. 1;

FIG. 3 shows a first modification of the block circuit diagram shown in FIG. 2;

FIG. 4 shows a second modification of the block circuit diagram shown in FIG. 2;

FIGS. 5 and 6, and FIG. 7 (consisting of FIGS. 7A and 7B) show modifications of the applicator shown in FIG. 1; and FIG. 8 (comprising FIGS. 8A and 8B) shows an example of a triple sound head for modified use in such ultrasonic scanning apparatus.

DETAILED DESCRIPTION

Referring to FIG. 1, an ultrasonic applicator comprises an ultrasonic sound head which is denoted by the reference numeral 1. The sound head 1 is situated in a container 2 which is filled with coupling liquid, for example water or oil. A diaphragm 3 of the liquid container 2 acts as an outlet window for ultrasonic waves produced by the sound head 1 in use. The sound head 1 contains, in all, two ultrasonic transducers 4 and 5 situated diametrically opposite one another in relation to an axis of rotation (pivoting) of the head 1. For driving the sound head 1 so as to produce an angular sweep displacement, there is provided a driving motor 6; the actual value of the sweep angle is determined by means of an actual-value angle generator 7. The sound head 1, the motor 6 and the angle generator 7 are operatively connected together by means of step-up gearing consisting of toothed wheels 9 to 12 and toothed belts 13 and 14.

Referring to FIG. 2, the sound head is again denoted by the reference numeral 1 and the driving motor 6 is diagrammatically shown. Associated with the actual-value angle generator 7 is a desired-value generator 15, from which a desired-value function signal $F_S(\rho)$ is applied, together with an actual-value function signal $F_I(\rho)$ from the actual-value generator 7, to a difference forming device 16. The running of the motor 6 is set to a desired value by means of a PID (proportional plus integral plus differential action) controller 17 and by means of a power stage 18. For exciting the sound head 1 so that it emits ultrasonic transmission pulses during a sector scanning phase of the ultrasonic scanning apparatus, there is employed, in a conventional manner, a high-frequency pulse generator 19 which supplies excitation pulses to the sound head 1 at a rate controlled by a master generator 20. Ultrasonic echo signals produced after the emission along a line in a sector field are reconverted to electrical signals by the sound head 1 and these electrical signals are finally applied, after amplification in a receiving amplifier 21, to an intensity modulating device (not shown) of a picture tube 22, in order to build-up an echo image display. A line triggering voltage necessary for building-up this image is supplied by a line sweep generator 23 and the necessary image sweep voltage is supplied by an image sweep generator 24. Basic devices for the production of these sweep voltages are a sine generator 25 and a cosine generator 26 respectively. The actual-value function signal $F_I(\rho)$ produced by the actual-value angle generator 7 is supplied to the inputs of the sine generator 25 and the cosine generator 26. The synchronization of the timing rate of the master clock 20 also takes place in dependence upon the actual-value function signal $F_I(\rho)$ via a comparator 27 (or an analog-to-digital converter) which controls the clock 20 so as to produce master clock pulses, starting from a particular amplitude of the actual-value function signal $F_I(\rho)$ with presettable variation steps up to a second amplitude of the actual-value function signal $F_I(\rho)$. For improving image quality, where necessary, the points of reversal of the sector pivoting displacement can also be controlled thereby. There is thus also obtained a fixed position of image lines on an image screen of the picture tube 22.

The desired function signal $F_S(\rho)$ produced by the desired-value generator 15 is a linear function signal in sawtooth form. The actual-value angle generator 7 is a linear generator, of which the angle determination range in the linear region extends at least beyond that of a sine or cosine generator or extends in the whole range similarly to the linear function produced by the desired-value generator 15. In this case, there is employed, as the actual-value generator 7, a field-plate potentiometer. Of course, other linear capacitive or inductive angle generators, or even linear resolvers may be employed. The described form of construction ensures linearity over a wide angle range, for example between 0° and ±40° or beyond this. The presetting of the linear functions has the advantage that the angular velocity of the pivoting displacement of the sound head 1 is constant over the whole pivoting angle range. This results in constant data (packing) density.

Referring to FIG. 3, again a sawtooth form of the curve of the desired-value function signal $F_S(\rho)$ at an input of the difference forming device 16 is shown. However, the actual-value angle generator 7 does not have a linear characteristic curve from the outset, because there is employed, as the actual-value angle generator 7, a sine (or cosine) angle generator 28 in combination with a succeeding linearizing device 29. The same linear effect is thus obtained as in the case of the linear angle generator 7 shown in FIG. 2.

FIG. 4 shows, on the other hand, a modification in the sense that there is preset, as the desired-value function signal $F_S(\rho)$ a sine (or cosine) function, i.e., a function having somewhat sharpened amplitudes as denoted by the reference numeral 30. In this case, there is then directly employed, for the actual-value angle generator 7, a sine (or cosine) angle generator 31 accordingly. The actual-value generator could also be an optical angle generator.

Of course, the spatial arrangement of the sound head 1, the motor 6 and the actual-value angle generator 7 in relation to one another may be appropriately modified. A first example of such a modification is illustrated in FIG. 5, in which the motor 6 is arranged to rotate the sound head 1 and the actual-value angle generator 7 about a common axis of rotation by means of a single, common toothed belt 32 which toothed wheels 33 and 34.

In FIG. 6 there is shown an example of an arrangement of the sound head 1, the motor 6, the actual-value angle generator 7 and toothed-belt gearing 35 to 40, enclosed in a housing 41 which is bent-over at an angle between an enclosure of the sound head 1 and a handpiece containing the motor 6 and the actual-value angle generator 7. The arrangement shown in FIG. 6 thus constitutes a form of construction which is particularly convenient for sector scanning and which is suitable not only for conventional pericardiac application, but also independently for suprasternal and subxiphoidal use.

In all of the arrangements described above, there is employed, as the drive motor 6, a so-called bell armature motor. Such a motor satisfies particularly well the conditions which must be met regarding lightness of running, rapid and reliable reversibility of rotation direction, and good controllability and regulatability. Bell armature motors suitable for use are commercially obtainable (for example, see the prospectus of the firm Faulhaber, DC-Micromotoren, Series 2225 to 3557).

Of course, there may, for example, be employed instead of a drive motor such as a bell armature motor, other rapidly reversible drives, more particularly electromagnetic drives. An example of an arrangement operating with such an electromagnetic drive 42 is shown in FIG. 7. The electromagnetic drive here consists of a permanent magnet 43 which is fixedly connected to a toothed belt 44. The control system controls the polarity and the flow of current through an exciter coil 45. The magnetic field set up as a result of the current flow exerts a force on the permanent magnet 43, the direction of which force depends upon the direction of the current flow. The actual-value angle generator 7 in the present case is again a rotational angle generator, but it can readily be replaced by a suitable displacement transducer.

All of the described arrangements thus have the advantage that the sound head 1 is no longer a part of the drive system; the drive system and the device for angle determination (i.e. the actual-value angle generator 7) can thus always be disposed outside the coupling liquid in the liquid container 2. The drive system is electronically regulated and so moves the sound head 4 that it follows a presettable time function in rocking (pivoting) displacement in a predetermined angle range. By means of the regulating system chosen, there is obtained a course of rocking displacement (actual value) which can, at any time, be made to follow any desired-value variation. It is thus possible to preset in any desired manner the angular velocity, and more particularly a constant angular velocity, image frequency and maximum sector angle. According to the arrangement chosen, the masses to be moved can be kept very small. In this way, it is ensured that the direction of rotation of the sound head 1 can be reversed as rapidly as desired by means of the drive system and that, more especially for heart-phase-triggered photography, the sound head 1 can very rapidly be brought out of a position of rest for a display run.

In all of the arrangements described, the sound head 1 always comprises two ultrasonic transducers 3 and 4, which are disposed diametrically opposite one another with respect to the pivoting axis of the sound head 1. These two transducers may differ with respect to frequency, focus position and diameter. With a 180° rotation, therefore, it is possible to change over to a new mode of operation by introducing a suitable transducer for the pivoting displacement in front of the diaphragm 3 of the ultrasonic applicator. Consequently it is possible merely by simple and rapid changeover to plumb different depths of the object being examined in accordance with different ultrasonic conditions. Therefore, replacement of the complete applicator is not necessary. If a field-plate potentiometer is used as the actual-value generator 7 in such a case, regulation without any discontinuity is obtained especially in the case of a double sound head with which a 180° rotational movement is required for running a new transducer into a scanning position, because a field-plate potentiometer has 180° periodicity of output function merely by virtue of simple polarity reversal. Of course, it is not necessary to provide two transducers; provided that examination with a single transducer is sufficient, the sound head 1 may, of course, be provided with only one transducer. It is naturally equally possible, where necessary, to increase the number of transducers to more than two. FIG. 8 illustrates diagrammatically, by way of example, a sound head 1 provided with a total of three ultrasonic transducers 46, 47 and 48 offset from one another at angles of 120°.

In order to ensure longer useful life of the motor 6 in the arrangements comprising a motor drive system, it is advantageous to utilize a range of rotation greater than the pivoting range of the sound head 1. For this purpose, it is merely necessary to choose a suitable mechanical transmission ratio 1:n of the sound head displacement to the motor rotation. For example, n=2 may be chosen, so that a rotation of the sound head 1 through 90° corresponds to a motor rotation through 180°.

The arrangement of individual component parts may as a whole be optimized according to requirements regarding convenience of handling and compactness. This may in some circumstances involve forms of construction in which the motor 6, the actual-value angle generator 7 and the sound head 1 are mounted on one axis of rotation. With such a form of construction, which is conceivable for suprasternal application, for example, it is possible to omit all or some of the additional step-up gearings between the individual devices.

It will be apparent that many modifications and variations may be effected without departing from the scope of the novel concepts and teachings of the present invention.

We claim as our invention:

1. Ultrasonic scanning apparatus comprising: an ultrasonic transducer arrangement; drive means arranged to pivotably displace the transducer arrangement within a predetermined angular range of at least plus or minus forty angular degrees; an actual-value generator for supplying a linear signal dependent upon the angular position of the transducer arrangement within the said range; a desired-value generator for supplying a signal representing a desired angular position of the transducer arrangement within the said range, with said signal representing said desired angular position being linear within said range; and closed loop control means for controlling the drive means in dependence upon such signals from the actual-value and desired-value generators; wherein the actual-value and desired-value generators are adapted to supply respective actual-value and desired-value signals having the same or similar linear wave forms over a relatively large signal range corresponding to said predetermined angular range of at least plus or minus forty angular degrees.

2. Ultrasonic scanning apparatus according to claim 1, further comprising a clock signal generator for controlling the transmission of ultrasonic pulses from the transducer arrangement, the clock signal generator being controlled in use by signals produced by the actual-value generator such that master clock pulses are produced by the clock signal generator at predetermined steps between first and second predetermined amplitudes of signals produced by the actual-value generator.

3. Ultrasonic scanning apparatus according to claim 1, wherein the drive means comprises a motor and step-up gearing arranged between the motor and the transducer arrangement.

4. Ultrasonic scanning apparatus according to claim 3, wherein the step-up gearing comprises a belt drive arrangement which is coupled, on the one hand, with the motor and, on the other hand, with the transducer arrangement and actual-value generator.

5. Ultrasonic scanning apparatus according to claim 4, wherein the belt drive arrangement comprises at least one toothed belt.

6. Ultrasonic scanning apparatus according to claim 5, wherein the or each toothed belt is coupled by a large number of teeth, on the one hand, with the motor, and on the other hand, with the transducer arrangement and actual-value generator.

7. Ultrasonic scanning apparatus according to claim 1, wherein the transducer arrangement comprises a plurality of ultrasonic transducers which are adapted for rotation by the drive means such that any one transducer can form an active transducer of the transducer arrangement at any instant.

* * * * *